United States Patent [19]

Vertesy et al.

[11] Patent Number: 5,506,202

[45] Date of Patent: Apr. 9, 1996

[54] INSULIN DERIVATIVES, A PROCESS FOR THE PREPARATION THEREOF, THE USE THEREOF, AND A PHARMACEUTICAL FORMULATION CONTAINING THEM

[75] Inventors: LászlóVertesy, Eppstein/Taunus; Karl Geisen; Günther J. Riess, both of Frankfurt am Main; Klaus Sauber, Bad Soden am Taunus, all of Germany

[73] Assignee: Hoechst Aktiengesellschaft, Frankfurt am Main, Germany

[21] Appl. No.: 442,296

[22] Filed: May 16, 1995

Related U.S. Application Data

[63] Continuation of Ser. No. 457,874, Dec. 27, 1989, abandoned.

[30] Foreign Application Priority Data

Dec. 29, 1988 [DE] Germany .......................... 38 44 211.6

[51] Int. Cl.$^6$ ............................ A61K 38/28; C07K 14/62
[52] U.S. Cl. ................................ 514/3; 530/303
[58] Field of Search ........................ 530/303; 514/3, 514/4; 435/68.1, 69.4

[56] References Cited

U.S. PATENT DOCUMENTS

| | | | |
|---|---|---|---|
| 4,343,898 | 8/1982 | Markussen | 435/71 |
| 4,400,465 | 8/1983 | Morihara et al. | 435/71 |
| 4,916,212 | 4/1990 | Markussen | 530/303 |
| 4,945,146 | 7/1990 | Kapmeyer et al. | |
| 4,946,828 | 8/1990 | Markussen | 514/3 |
| 4,959,351 | 9/1990 | Grau | 514/4 |

FOREIGN PATENT DOCUMENTS

| | | |
|---|---|---|
| 0227938 | 3/1986 | European Pat. Off. |
| 0229998 | 4/1986 | European Pat. Off. |
| 0286956 | 7/1986 | European Pat. Off. |
| 0289936 | 9/1986 | European Pat. Off. |
| 0195691 | 9/1986 | European Pat. Off. ............ 514/3 |
| WO88/02005 | 3/1988 | WIPO ................................ 514/3 |
| WO90/11299 | 10/1990 | WIPO. |

OTHER PUBLICATIONS

Blundell, T. et al., *Advances in Protein Chemistry*, Ed. Anfinsen & Edsall & Richards, 1972, pp. 340–345.
Creighton, T., *Proteins*, 1984, p. 428.
"Molecular Basis of INsulin Action: Contributions of Chemical Modifications and Synthetic Approaches", Zahn et al., pp. 468–475, presented at 50th Anniv.Insulin Symposium, Indiana, Oct. 1971.
"Kristallisiertes Arginyl$^A$–insulin", Weinert et al.; Hoppe-–Seyler's Z. Physiol. Chem. Bd. 352, S. 719–724, May 1971.
"Amino Acid Sequences of Insulins", Leslie F. Smith; Section III. The Molecular Basis of Action, pp. 457–458, presented at 50th Anniv. Insulim Symposium, Indiana, Oct. 1971.
Seipke et al., "High–Pressure Liquid Chromatography (HPLC) of Proteins", Angew. Chem. Int. Ed. Engl. 25 (1986), 535–552.
Rosen et al., "Binding of Insulin to Bovine Liver Plasma Membrane", Biochem. J. (1980) 186, 945–952.
Thim et al., "Secretion and Processing of Insulin Precursors in Yeast", Proc. Natl. Acad. Sci. USA, vol. 83, pp. 6766–6770, Sep. 1986, Biochem.

*Primary Examiner*—Howard E. Schain
*Assistant Examiner*—Benet Prickril
*Attorney, Agent, or Firm*—Finnegan, Henderson, Farabow, Garrett & Dunner

[57] ABSTRACT

New insulin derivatives, a process for their preparation and use, and a pharmaceutical formulation containing them are disclosed. The derivatives contain the basic amino acid arginine at the amino-terminal position of the insulin A-chain, and various amino acid substitutions at the carboxyl terminus of the insulin B-chain. The compounds are suitable for the treatment of diabetes mellitus, have a delayed profile of action and are very well tolerated.

18 Claims, 5 Drawing Sheets

FIG. 2 (PTF 1)

FIG. 2a (PTF 1)

Asp-NH₂ – Thr – Thr – Val – Ser – Glu – Pro – Ala – Pro – Ser(10) – Cys-Val-Thr-Leu-Tyr-Gln-Ser-Trp – Arg – Tyr-Ser-Gln-Ala-Asp-Asn-Gly-Cys – Ala – Glu – Thr(30) – Val – Thr – Val – Lys – Val – Val – Tyr – Glu – Asp – Asp(40) – Thr – Glu – Gly – Pro – Ser – Leu – Asn – Ser – Ala – Arg(50) – Phe-Val-Asn-Gln-His-Leu-Cys-Gly-Ser-His-Leu-Val-Glu-Ala(60)

(loop) Gly-Gly-Gly-Leu-Glu-Val-Gln-Gly-Val-Gln-Pro-Asp(90) ... Pro – Gly – Ala(100) – Gly – Ser – Leu – Gln – Pro – Leu – Ala – Leu – Glu – Gly(110) – Ser – Leu – Gln – Lys – Arg – Gly – Ile-Val-Glu-Gln-Cys-Cys-Thr-Ser-Ile-Cys(120)

Asn-OH(136) – Cys – Tyr – Asn – Glu – Leu – Gln(130) – Tyr – Leu – Ser – Cys

Right column: Tyr – Phe – Phe – Gly – Arg – Glu – Gly(70) – Cys – Val – Leu – Tyr – Leu – Thr(80) – Lys – Pro – Thr – Arg – Arg – Glu – Ala – Glu Disulfide bonds: S—S between Cys residues indicated.

INSULIN DERIVATIVES, A PROCESS FOR THE PREPARATION THEREOF, THE USE THEREOF, AND A PHARMACEUTICAL FORMULATION CONTAINING THEM

This application is a continuation of application Ser. No. 07/457,874 filed Dec. 27, 1989, now abandoned.

DESCRIPTION

As is known, considerable amounts of insulin and insulin derivatives are required for the treatment of the disease diabetes mellitus, and some of them are also produced on the industrial scale. Despite the considerable number of existing insulin formulations and modifications with different profiles of action, there is still a need, because of the differences between organisms with inter- and intraindividual variations, for further insulin products with yet different properties and action characteristics.

Insulin derivatives with a delayed action are described, for example, in EP-B 132,769 and EP-B 132,770. These are specifically derivatives with a basic modification in position B 31 of the insulin B chain of the following formula I:

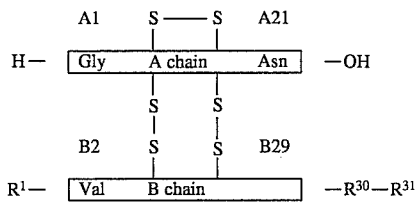

in which $R^1$ denotes H or H-Phe, $R^{30}$ represents the residue of a neutral, genetically encodable L-amino acid, and $R^{31}$ represents a physiologically acceptable organic group which is basic in nature and has up to 50 carbon atoms, in whose structure 0 to 3 α-amino acids are involved, and whose terminal carboxyl functionality, which is present where appropriate, can be in the free form, as ester functionality, as amide functionality, as lactone or reduced to $CH_2OH$.

Characteristic of these insulin derivatives is an isoelectric point between 5.8 and 8.5 (measured by isoelectric focusing). The isoelectric point—which is shifted into the neutral range by comparison with the isoelectric point of the unmodified native insulin or proinsulin (at pH = 5.4)—is determined by the additional positive charge(s) located on the surface of the molecule as a result of the basic modification. This makes these insulin derivatives with a basic modification less soluble in the physiological neutral range than is, for example, native insulin or proinsulin, which are normally in dissolved form in the neutral range.

The delaying or depot action of the insulin derivatives with a basic modification, of the formula I, derives from their sparing solubility at the isoelectric point. The redissolution of the insulin derivatives under physiological conditions is said to be achieved by elimination of the additional basic groups, which occurs, depending on the derivative, due to trypsin or trypsin-like and/or carboxypeptidase B or carbexypeptidase B-like and/or esterase activity. The groups which are eliminated in each case are either purely physiological metabolites or else readily metabolizable, physiologically acceptable substances.

The abovementioned depot principle as a result of basic modification of the insulin has subsequently been utilized further by the provision and corresponding use of other insulin derivatives with a basic modification— principally within the A and B chains; cf. for example EP-A 0,194,864 and EP-A 0,254,516.

There are also known some insulin derivatives with a basic modification in the extension of the A-chain beyond the A1-position; cf. P. Rösen et al., Biochem. J. (1980), 186, 945–952. As such insulin derivatives having basic aminoacids as modifying components are described in said literature specifically Lys-Arg-Gly$^{A1}$-bovine insulin, Arg-Gly$^{A1}$-bovine insulin, Arg-Arg-Gly$^{A1}$-bovine insulin, and Arg-Arg-Arg-Gly$^{A1}$-bovine insulin.

These insulin derivatives are said to have a considerably minor biological activity in comparison with unmodified insulin; cf. particularly Table 1 on page 947 of the literature-article. Nothing is, however, disclosed in said article about an eventual depot-activity.

In the attempt to extend further, and make utilizable, the before-mentioned depot principle for the treatment of the disease diabetes mellitus in an advantageous manner, a new group of insulin derivatives with a basic modification has now been found; these are insulin derivatives of the formula II hereinafter, at whose A0 position the basic amino acid arginine is located:

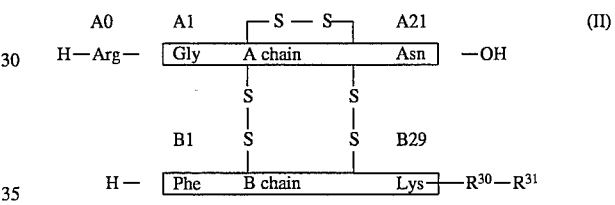

in which a) $R^{30} + R^{31}$ together=OH or b) $R^{30}$=residue of a neutral, genetically encodable L-amino acid and $R^{31}$ =OH or a physiologically acceptable organic group which is basic in nature and has up to 50 carbon atoms, An whose structure 0 to 3 α-amino acids are involved, and whose terminal carboxyl functionality, which is present where appropriate, can be in the free form, as ester functionality, as amide functionality, as lactone or reduced to $CH_2OH$, except the case, in which at the same time $R^{30}$= Ala, $R^{31}$=OH, and the A- and B-chain are the sequences of bovine insulin [i.e. Arg$^{A0}$-bovine insulin].

The physiologically tolerated salts (such as, for example, alkali metal or ammonium salts) of these insulin derivatives are included An the invention.

BRIEF DESCRIPTION OF THE DRAWINGS

FIGS. 2 and 2a respectively depict the structural formula and amino acid sequence of fusion protein PTF1.

Figure 1:
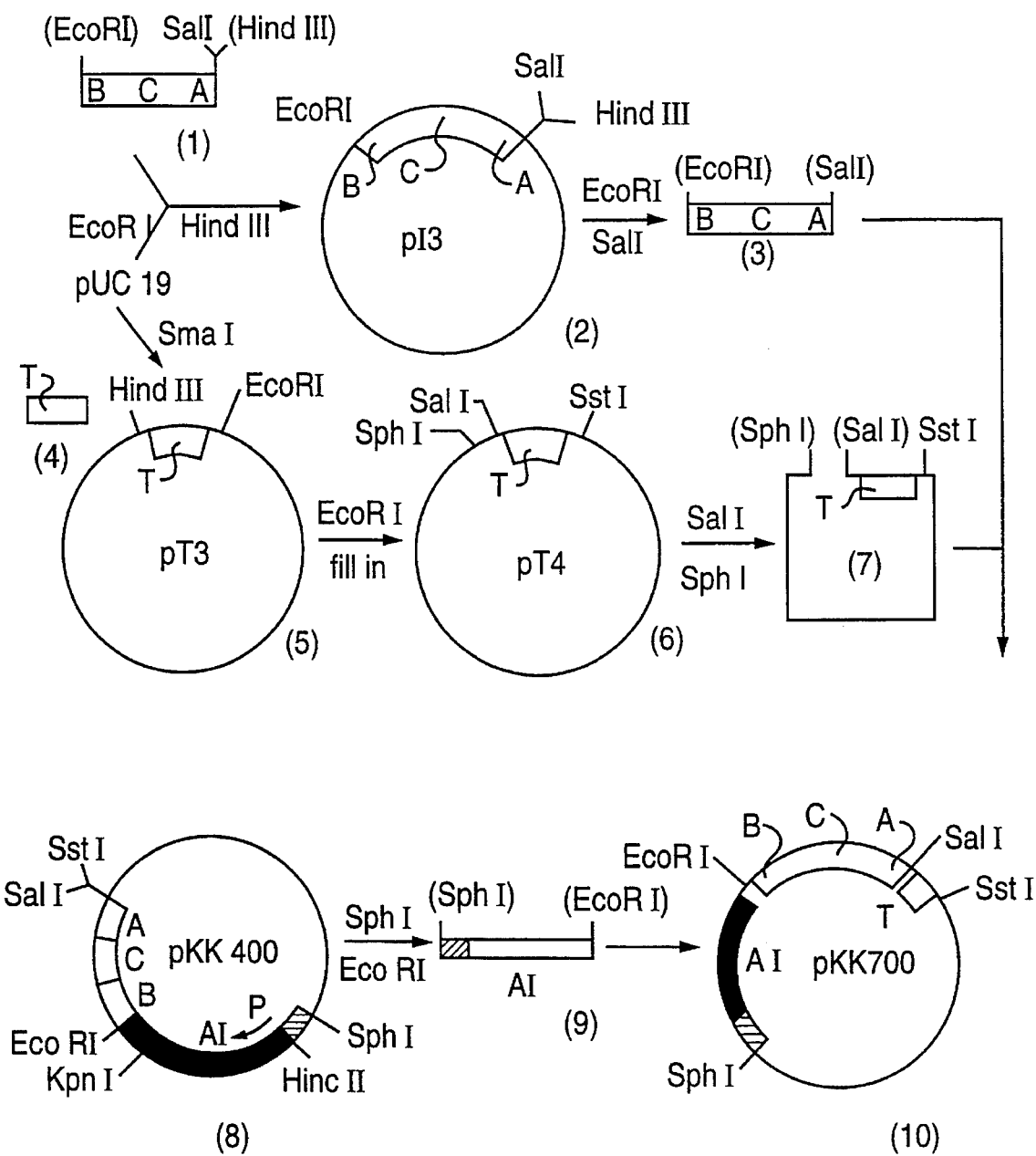
FIG. 1 depicts a gens construction used to prepare the precursor compound of formula (III)

The new insulin derivatives have, as a result of their basic modification in the A0 position—like the known insulin derivatives with a basic modification too—a delayed profile of action and—by comparison with the known insulin derivatives with a basic modification—distinct advantages with regard to tolerability in the body; it is also—in view of the before-mentioned article of P. Rösen et al.—completely surprising that their biological activity corresponds to that of native insulin.

a) The compounds of the formula II with $R^{30}$+ $R^{31}$ together=OH are the corresponding $Ag^{A0}$, des-B30-insulins; these compounds are particularly preferred.

b) Alternatively, $R^{30}$ in formula II can also be the residue of a neutral, genetically encodable L-amino acid and $R^{31}$ =OH or a corresponding physiologically acceptable organic group which is basic in nature and has up to 50 carbon atoms.

Neutral, genetically encodable L-amino acids—for $R^{30}$-are Gly, Ala, Ser, Thr, Val, Led, Ils, Asn, Gln, Cys, Met, Tyr, Phe and Pro; Ala, Thr and Ser are preferred, in particular only Thr.

If $R^{31}$=OH, the resulting insulin derivatives differ from the corresponding insulins only by the modification in the A0 position (Arg)—in the case of the particularly preferred neutral genetically encodable L-amino acid Thr and of the A and B1 to B29 chain=sequences of human insulin) this is $Arg^{A0}$-human insulin.

If $R^{31}$=a corresponding physiological acceptable organic group which is basic in nature and has up to 50 carbon atoms, the resulting insulin derivatives differ from the insulin derivatives with a basic modification according to the publications EP-B 132,769 and EP-B 132,770 mentioned in the introduction in principle only by the additional Arg residue in the A0 position.

If no α-amino acids are involved in the structure of $R^{31}$, examples of suitable basic groups for this radical are the following:

Amino- $(C_2-C_6)$-alkoxy, $(C_1-C_4)$-alkylamino-$(C_2-C_6)$-alkoxy, di-$(C_1-C_4)$-alkylamino-$(C_2-C_6)$-alkoxy, tri-$(C_1-C_4)$-ammonio-$(C_2-C_6)$-alkoxy, amino-$(C_2-C_6)$-alkylamino, [$(C_1-C_4)$-alkylamino]-$(C_2-C_6)$-alkylamino, di-$(C_1-C_4)$-alkylamino-$(C_2-C_6)$-alkylamino or [tri-$(C_1-C_4)$-alkylamino] -$(C_2-C_6)$-alkylamino, in particular —O— $[CH_2]_p$—$NR_2$, —O— $[CH_2]_p$—$N^{\oplus}R_3$, —NH— $[CH_2]_p$—$NR_2$ or —NH— $[CH_2]_p$—$N^{\oplus}R_3$, in which p=2 to 6 and R is identical or different and represents hydrogen or $(C_1-C_4)$alkyl.

When up to 3 α-amino acids are involved in the structure of $R^{31}$, these are primarily neutral or basic naturally occurring L-amino acids and/or the D-amino acids corresponding to the latter. Neutral naturally occurring amino acids are, in particular, Gly, Ala, Set, Thr, Val, Led, Ile, Ash, Gln, Cys, Met, Tyr, Phe, Pro and Hyp. Basic naturally occurring amino acids are, in particular, Arg, Lys, Hyl, Orn, Cit and His. If only neutral α-amino acids are involved, the terminal carboxyl functionality thereof cannot be free—in order for $R^{31}$ to be basic in nature; on the contrary, in this case the carboxyl functionality must be amidated or esterified with a basic group, suitable basic groups of this type being, for example, the basic groups mentioned above—for the case where no α-amino acids are involved in the structure of $R^{31}$. It is of course also possible for these basic ester or amide groups to block the carbexyl functionality of basic α-amino acids. Neutral ester or amide groups such as, for example, $(C_1-C_6)$-alkoxy, $(C_3-C_6)$-cycloalkoxy, $NH_2$, $(C_1-C_6)$-alkylamino or di-$(C_1-C_6)$-alkylamino may also be suitable for blocking the carbexyl functionality of the basic α-amino acids—if the blocking is desired.

Of course, the terminal carbexyl functionality can be in lactone form only if the terminal amino acid is a hydroxy amino acid.

It is additionally possible for the terminal carboxyl functionality to be reduced to $CH_2OH$.

$R^{31}$ is preferably composed of 1, 2 or 3 of the abovementioned basic naturally occurring amino acids; $R^{31}$ is particularly preferably Arg—OH or Arg—Arg—OH.

The particularly preferred meaning of $R^{31}$ is preferably combined with $R^{30}$= Ala, Thr or Ser, in particular only Thr. The results with $R^{30}$=Thr and the A chain and B1 to B29 chain=sequences of human insulin are $Arg^{A0}$, $Arg^{B31}$—OH—human insulin and $Arg^{A0}$, $Arg^{B31}$, $Arg^{B32}$—OH—human insulin.

The A chain and the B1 to B29 chain in formula II can in principle be the sequences of all possible insulins; however, they are preferably the sequences of human, pork or beef insulin, in particular the sequences of human insulin (which are identical to the A1 to A21 and B1 to B29 sequences of pork insulin).

The isoelectric point of the insulin derivatives of the formula II is between 5.5 and 9.0 (measured by isoelectric focusing).

The insulin derivatives of the formula II can be prepared by a) contacting an insulin product of the formula III or

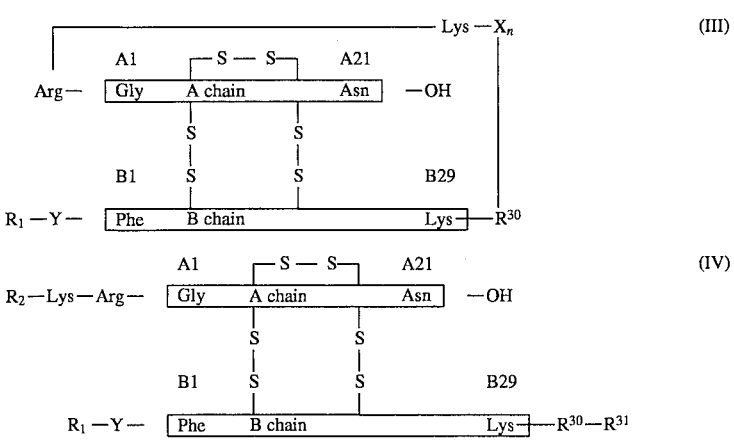

in which

X=residues of identical or different genetically encodable L-amino acids,

Y=Lys or Arg, n=0 or integer from 1–60, $R_1$ and $R_2$=OH or optionally derivatized—residues of a natural amino acid, or optionally derivatized—peptide residues composed of 1–90, preferably 70–80, natural amino acids, $R^{30}$ and $R^{31}$ have the same meaning as in formula II, and the A and B(1-29) chains preferably have the sequences of human, pork or beef insulin, in particular of human or pork insulin, with lysyl endopeptidase, there being cleavage of the bonds at the C-terminal end of the Lys residues, and where appropriate—i.e. when Y=Arg—also being mixed with trypsin or a trypsin-like protease, there being elimination of the moiety $R_1$-Y from the B chain, and an $Arg^{A0}$, des-B30-insulin derivative of the formula IIa being produced, and/or b) for the preparation of an insulin derivative of the formula IIb, reacting an $Arg^{A0}$, des-B30-insulin derivative of the formula IIa in the presence of lysyl endopeptidase or trypsin or of a trypsin-like protease with a compound of the formula V $$HR^{30}\text{---}R^{31} \qquad (V),$$

in which $R^{30}$ and $R^{31}$ have the meanings specified for formula IIb, and in which free COOH, OH, SH, $NH_2$, guanidino and/or imidazole functionalities which are present can be in a form protected in a manner known per se, and subsequently eliminating, in a manner known per se, protective groups which are present where appropriate, or by c) reacting an $Arg^{A0}$, des-octapeptide (B23-30)-insulin of the formula VI

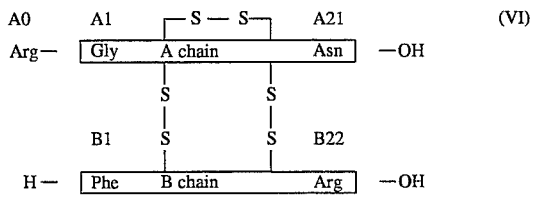

in the presence of trypsin or a trypsin-like protease with a compound of the formula VII $$\text{H-Gly-Phe-Phe-Tyr-Thr-Pro-Lys-}R^{30}\text{-}R^{31} \qquad (VII)$$

in which $R^{30}$ and $R^{31}$ have the meanings specified for formula II under a) and b), it being possible for free COOH, OH, SH, $NH_2$, guanidino and/or imidazole functionalities which are present to be in a form protected in a manner known per se, and subsequently eliminating, in a manner known per se, protective groups which are present where appropriate, or by d) reacting insulin (derivatives) of the formula II'

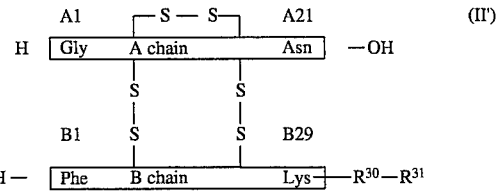

in which $R^{30}$ and $R^{31}$ have the same meaning as in Formula II ( a/b ), and whose reactive amino groups—with the exception of the amino group on GlyAL— are in a form protected in a known manner, with arginine whose amino groups are likewise protected in a known manner and whose COOH group is in activated form where appropriate, and subsequently eliminating, in a known manner, the protective groups which are present.

The insulin derivatives of the formula II which are obtained can, if desired, be converted in a known manner into corresponding physiologically tolerated salts.

The abovementioned process variants a) to d) are explained in detail as follows:

Variant a):

Explanation of the formulae of the starting materials III and IV:

The symbol X occurs in formula III and denotes identical or different genetically encodable amino acids. The following amino acids (each in the L form) are genetically encodable: Gly, Ala, Ser, Thr, Val, Leu, Ile, Asp, Asn, Glu, Gln, Cys, Met, Arg, Lys, His, Tyr, Phe, Trp, Pro.

Natural amino acids—in the or for the radicals $R_1$ and $R_2$ in formula IV—are, inter alia, Gly, Ala, Set, Thr, Val, Leu, Ile, Asn, Gln, Cys, Met, Tyr, Phe, Pro, Hyp, Arg, Lys, Hyl, Orn, Cit and His.

The amino acids and peptide chains can be derivatized in a customary manner—that is to say provided with the protective groups customary in peptide chemistry for the amino and/or carboxyl groups.

The compounds of the formula III and their precursors without disulfide bridges are preferably prepared by a genetic engineering process, in particular that disclosed in EP-A 0, 289,936. The precursors described therein are fusion proteins composed of monkey proinsulin with (optionally truncated) tendamistat linked via a short peptide bridging member. Fusion proteins of this type can be expressed in Streptomycetes cells and secreted into the culture medium, from which they can be isolated particularly easily. German Patent Application P 38 37 273.8 proposes specially designed fusion proteins in which the A and B chains of TNS the insulin have a correct disulfide-bridge linkage and the C peptide is truncated to the amino acid lysine. It is possible entirely in analogy to this to prepare a fusion protein in which the C chain is truncated to the amino acid arginine. A particularly advantageous modification of the proposed process comprises, however, attaching a codon for the amino acid arginine to the codon for lysine which is present in the gene for the fusion protein, so that the result therefore is à fusion protein whose C chain is composed of Lys-Arg.

Corresponding fusion proteins can also be prepared by other processes known per se, for example those of EP-A 0,227,938, EP-A 0,229,998, EP-A 0,286,956 and EP-A 0,290,005 in E. coli.

The compounds of the formula IV and their precursors are prepared by forming the individual chains

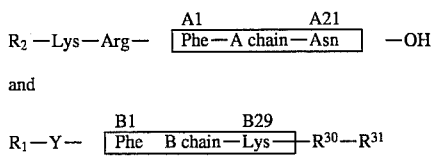

and separately, preferably by genetic engineering, for example in accordance with the processes of EP-A 0,289,-936, EP-A 0,286,956, EP-A 0,229,998, EP-A 0,227,938 and EP-A 0,290,005. Subsequently, the chains, provided with protective groups in suitable form where appropriate, are linked by processes known per se. There are various descriptions of processes of this type in the literature, for example by P. G. Katsoyannis et al. in J. Am. Chem. Soc. 85, 2863–2865 (1963).

To carry out process variant a), the compound of the formula III or IV is then contacted with lysyl endopeptidase, for example from Lysobacter enzymogenes, in aqueous solution or suspension. The amount (by weight) of the pure enzyme which is employed is preferably about 1/50 to 1/10,000, in particular between about 1/100 to 1/1,000, of the amount of the starting insulin product of the formula III or IV.

The pH of the reaction mixture can varywithin relatively wide limits; however, the range between about 5.5 and 10.5 is preferred, in particular between about 7 and 9.

The reaction temperature is preferably room temperature.

The reaction time depends principally on the amount of enzyme and is from a few minutes to several days, preferably a few hours.

The enzyme lysyl endopeptidase cleaves peptide chains which contain the amino acid lysine at the carboxyl side of the lysine. Hence, the result from compounds of the formulae III and IV is—when Y=Lys—$Arg^{A0}$, des-B30 insulin which can be purified by methods known per se. When Y=Arg in the starting compounds III and IV, the group $R_1$—Y—Phe is retained at the N-terminal end of the B chain. The elimination of the radical $R_1$—Y (=$R_1$—Arg) from the B chain must then be carried out by subsequent cleavage with trypsin or a trypsin-like protease, which can take place without or else after the isolation of the intermediate product ($R_1$—Arg—Phe—...). The isolation and purification of the $Arg^{A0}$, des-B30-insulin derivative which is formed is then again carried out by known methods.

In the literature, lysyl endopeptidase is often included among the trypsin-like endopeptidases and is often mentioned in addition to them too. The latter view is chosen in the present case.

Variant b):

This is a coupling reaction in which the compound of the formula V is linked to the $Arg^{A0}$, des-B30-insulin derivative (of the formula IIa)—obtained by process variant a) for example—to give an $Arg^{A0}$-insulin or -insulin derivative of the formula IIb. This takes place by methods known per se, in analogy to that described, for example for transamidations in EP-B 0,056,951.

When starting materials which have been provided with protective groups have been employed in this case, the latter should be eliminated again at the end in a known manner.

Variant c):

The starting material of the formula VI can be obtained in analogy to the starting materials for variant a). The linkage with the peptide of the formula VII takes place in a manner known per se, as described, for example, by Inouye et al. in J. Am. Chem. Soc. 101, 751–752 (1979).

In this case too—when starting materials provided with protective groups have been employed—the protective groups should be eliminated again at the end.

Variant d):

This is a linkage of arginine to an insulin derivative of the formula II' in the A0 position.

Suitable protective groups for the amino groups both in the insulin derivative of the formula II'—in which, however, the amino group of the $Gly^{AL}$ must remain unprotected—and in the amino acid arginine are the protective groups customary in peptide chemistry for amino groups, such as, for example, the benzyloxycarbonyl, the tert.-butyloxycarbonyl or the fluoren-9-yl-methoxycarbonyl group.

If the starting arginine is employed with a free carboxyl group, it is expedient to carry out the linkage with $Gly^{A1}$ using carbodiimide. Otherwise, it is expedient to "activate" the carboxyl group, that is to say convert it before the actual reaction into an activated form such as, for example, the acid halide or azide form.

The insulin derivatives of the formula II (a/b) and the physiologically tolerated salts thereof are primarily used as active substances for pharmaceutical formulations for the treatment of diabetes mellitus.

Hence the invention also relates to a pharmaceutical formulation which contains at least one insulin derivative of the formula II and/or at least one of the physiologically tolerated salts thereof in dissolved, amorphous and/or crystalline, preferably in amorphous and/or crystalline—form.

Insulin derivatives of the formula II which are preferred for this pharmaceutical formulation are
$Arg^{A0}$, Des-B30-human insulin,
$Arg^{A0}$-human insulin
$Arg^{A0}$, $Arg^{B31}$, $Arg^{B32}$, OH-human insulin and
$Arg^{A0}$, $Arg^{B31}$, $Arg^{B32}$, Oh-human insulin
and the physiologically tolerated salts thereof.

The pharmaceutical formulation is preferably a solution or suspension for injection purposes with a pH between about 3.0 and 9.0, preferably between about 5.0 and 8.5, which contains a suitable tonicizing agent, a suitable preservative and, where appropriate, a suitable buffer, as well as, where appropriate, a certain zincion concentration or another depot principle such as, for example, protamine sulfate, all, of course, in sterile aqueous solution or suspension. The totality of the ingredients of the formulation apart from the active substance forms the formulation vehicle.

Examples of suitable tonicizing agents are glycerol, glucose, mannitol, NaCl, calcium or magnesium compounds such as, for example, $CaCl_2$, $MgCl_2$, etc.

Examples of suitable preservatives are phenol, m-cresol, benzyl alcohol and/or p-hydroxybenzoic esters.

Examples of buffer substances which can be used, in particular for adjusting a pH between about 5.0 and 8.5, are sodium acetate, sodiumcitrate, sodiumphosphate etc. Otherwise suitable for adjusting the pH are physiologically acceptable dilute acids (typically HCl) or alkalis (typically NaOH).

When the formulation contains zinc, a content of about 1 µg to 2 mg, in particular of about 5 µg to 200 µg, of zinc/ml is preferred.

It is also possible to admix, for the purpose of altering the profile of action of the formulation according to the invention, other modified (cf. EP-B 132,769 and EP-B 132,770) and/or unmodified insulins, preferably beef, pork or human insulin, in particular human insulin.

Preferred concentrations of active substances are those corresponding to about 1 to 1500, further preferably about 5 to 1000, and in particular about 40 to 400, international units/ml.

The pharmaceutical formulation is prepared by converting at least one insulin derivative of the formula II and/or at least one of the physiologically tolerated salts thereof, where appropriate together with other modified and/or unmodified insulins or derivatives thereof, with a physiologically acceptable vehicle and, where appropriate, with suitable additives and auxiliaries, into a suitable dosage form.

The invention is now explained in more detail by the examples which follow.

Preparation of $Arg^{A0}$, des-B30-Human Insulin by Process Variant a)

A) Preparation of a Starting Material of the Formula III:

A1)

The synthetic gene (1) depicted in FIG. 1 is chemically synthesized in a manner known per se by the phosphoramidire method. The preference of Streptomycetes for G and C was taken into account in the choice of codons. As with the gene coding for monkey proinsulin in EP-A 0,289,936 (Table 2 therein), the gene (1) shown in FIG. 1 also has at the 5' end a protruding sequence typical of the restriction enzyme EcoRI. Downstream of the structural gene there are two stop codons and a linker sequence with the recognition site for the enzyme SalI. At the 3' end there is the protruding sequence corresponding to the restriction enzyme HindIII.

The commercially available plasmid pUC19 is cut with the enzymes EcoRI and HindIII, and the synthetic gene (1) shown in FIG. 1 is ligated in. This results in the plasmid pI3 (2). After amplification, the synthetic gene is cut out as fragment (3) with the enzymes EcoRI and SalI and employed for the construction described hereinafter.

Figure 2:
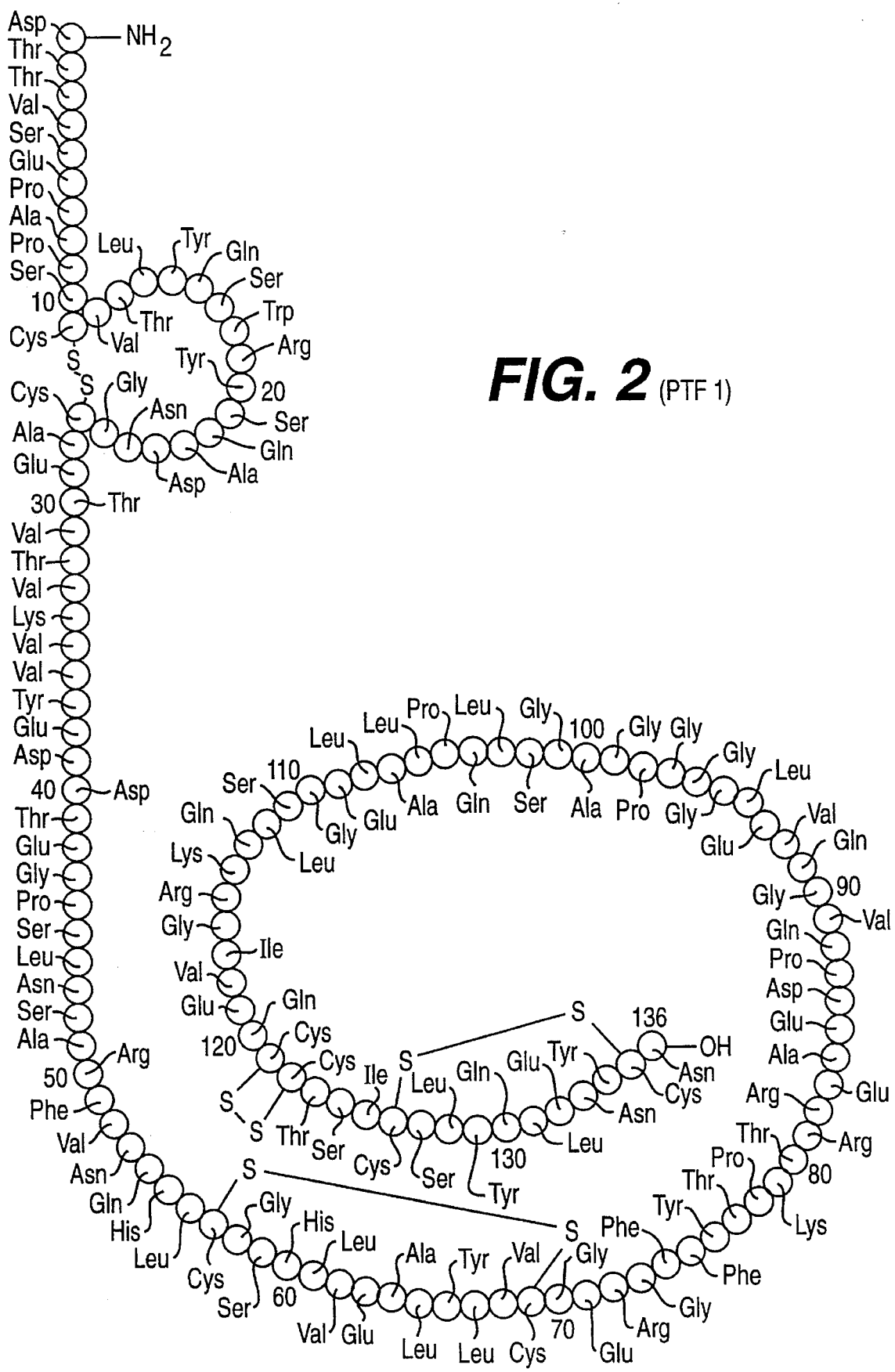

The plasmid pUC19 is completely digested with SmaI and ligated to the terminator sequence (4) depicted in FIG. 2. Plasmids which contain this sequence in the correct orientation are called pT3 (5). This plasmid (5) is opened with EcoRI and the cleavage site is filled in with DNA polymerase (Klenow fragment). Religation results in the plasmid pT4 (6). This plasmid is opened with the enzymes SalI and SphI, and the large fragment (7) is isolated.

The plasmid pKK400 (8) (cf. EP-A-0,289,936, FIG. 4, (20)) is cut with SphI and EcoRI, and the small fragment (9) with the tendamistat gene is isolated.

Ligation of fragments (3), (7) and (9) results in the plasmid pKK700 (10), in which the tendamistat sequence is followed by the bridging member coding for 12 amino acids Phe Asn Ala Met Ala Thr Gly Asn Ser Asn Gly Lys
TTC AAT GCG ATG GCC ACC GGG ATT TCG AAC GGC AAG
AAG TTA CGC TAC CGG TGG CCC TAA AGC TTG CCG TTC
                                EroRI and, after this, the gene for the modified proinsulin. The arrangement is checked for correctness by cutting with SphI and SstI, there being obtained a fragment of 826 bp from the plasmid about 3.5 kb in size. DNA sequencing by the dideoxy method confirms that the sequence is correct.

Gene constructions in which the Lys acting as C peptide is replaced by Arg are prepared analogously. For this purpose, the triplet coding for Lys is replaced by CCC. The plasmid pI5 and, from this, the vector pKK800 are obtained analogously.

FIG. 1 explains the gene construction by the method A1 described here; it is not true to scale.

A2)

In analogy to the rector pGF1 described in EP-A 0,289,936, the expression plasmids pGF4 and pGF5 are prepared from the vectors pKK700 and pKK800. For this purpose, the inserts of 826 and 823 bp, respectively, are isolated from the vectors pKK700 and pKK800 by double digestion of each with SphI and SstI, and these DNA fragments are ligated into the expression plasmid pIJ702 which has been cleaved with the same enzymes. The ligation mixture is transformed into S. lividans TK 24, and the plasmid DNA is isolated from thiostrepton-resistant transformants which show tendamistat activity (plate test). Allpositive clones contain the insert from pKK700 or pKK800 employed.

The encoded fusion proteins can be expressed in a known manner. When the transformed strain S. lividans TK 24 is incubated at 28° C. in a shaken flask for four days and the mycelium is separated from the culture solution by centrifugation, the fusion protein can be detected in the clear solution as follows:

10 to 100 µl of solution are mixed with 20 to 200 µl of 15% strength trichloroacetic acid, and the precipitated protein is collected by centrifugation, washed and taken up in SDS-containing sample buffer (U. Laemmli, Nature 227 (1970) 680–685). Incubation at 90° C. for 2 minutes is followed by fractionation by electrophoresis on a 10–17% SDS polyacrylamide gel. A protein of molecular weight 15 kD is obtained, that is to say in the expected molecular weight range for the fusion protein composed of tendamistat and proinsulin. The fusion protein—a product covered by formula III—reacts both with antibodies against tendamistat end with antibodies against insulin.

A3) Strain maintenance and fermentation

Strains of S. lividans which contain the recombinant plasmid pGF4 from A2) are streaked onto nutrient agar plates which contains as complex nutrient medium R2YE medium (Hopwood etal., Genetic Manipulation of Streptomyces: A Laboratory Manual; John Innes Foundation, Norwich, England; 1985) and are incubated at temperatures from 25° to 30° C., preferably at 28° C. To stabilize the plasmids the sporulation medium contains as selection additive thiostrepton in a concentration of 20 µg/ml. After sporulation has taken place, the spores are harvested by placing a layer of water in the plates and treating with ultrasound. Titration of the spores is followed by preparation of a solution of $10^{10}$ spores/ml in 20% aqueous glycerol and storage at –20° C.

A4) Setting up cultures

Used as preculture medium is a complex nutrient medium composed of soybean meal (20 g/l), glucose (10 g/l), corn starch (2 g/l), urea (1 g/l), ammonium nitrate (1 g/l), malt extract (5 g/l) and $KH_2PO_4$ (2 g/l) and thiostrepton as selection additive in a concentration of 10 to 50 µg/l. $5 \times 10^9$ spores/l of final volume are employed as inoculum. The preculture is shaken at 220 rpm and at 27° C. and, after 60 hours, transferred An a dilution of 1:20 into the main culture.

Used as main culture is a complex nutrient medium whose pH is adjusted to 7.2 and which is composed of soluble starch (40 g/l), corn steep liquor (4 g/l), skim milk powder (7 g/l), glucose (10 g/l), $(NH_4)_2SO_4$ (12 g/l) and soybean meal (4 g/l).

The fermentation is carried out in customary stirred tank fermenters, aerating at 0.5 vvm and stirring at 200–240 rpm at 25° C. for 48 hours. The subsequent treatment of the culture solution after the fermentation is complete comprises the cell pellets being separated from the culture liltrate by suction filtration through a closed funnel in order to avoid aerosol formation. The clear culture liltrate contains the desired fusion protein.

The yield of fusion protein is up to about 20% higher when the pH of the main culture solution is maintained constant at 6.5 to 7.2, preferably 6.9, with NaOH and 3% phosphoric acid.

A5) Isolation of the fusion protein PTF1

30 l of culture solution from the Streptomyces lividans fermentation for producing the plasmid-encoded fusion protein obtained in accordance with the process of E-PA 0,289, 936, PTF1 hereinafter, are mixed with 4.0 g of p-chlorometa-cresol and left to stand for 30 minutes to kill the culture. After this time, the biomass is separated off on a filter press, and the liltrate is adjusted to pH 4.0 with trichloroacetic acid while cooling. After 3 hours, the precipitate is collected by centrifugation. Subsequent stirring with 10 times the amount of acetone results in removal of fats. The acetone phase is filtered off and discarded. The protein pTF1 is dissolved by suspending in 6 molar urea solution and adjusting the pH to 7.5, and remaining insoluble material is removed by a renewed centrifugation. The clear liquid phase can be loaded directly onto a Q-Sepharose column which has been equilibrated with tris/HCl buffer (pH 7.5) in 3 molar urea. The column (5 cm in diameter, 15 cm high) contains 300 ml of ion exchanger. Elution is carried out with a 0 to 0.5 molar NaCl/urea solution. The PTF1-containing fractions are collected and dialyzed to remove salts. 300 mg of the enriched product are then loaded onto a macrobere Nucleosil 120-10 C4 HPLC column and eluted with 0.1% strength trifluoroacetic acid to which increasing amounts of acetonitrile are added. The protein PTF1 is detached from the column with 36% strength acetonitrile. The solvent is removed from the corresponding fractions in vacuo. 186 mg of pure PTF1 result. The structural formula is depicted in FIG. 2 (copy of the amino acid sequences=FIG. 2a).

A6) Refolding of the fusion protein PTF1

Figure 3:
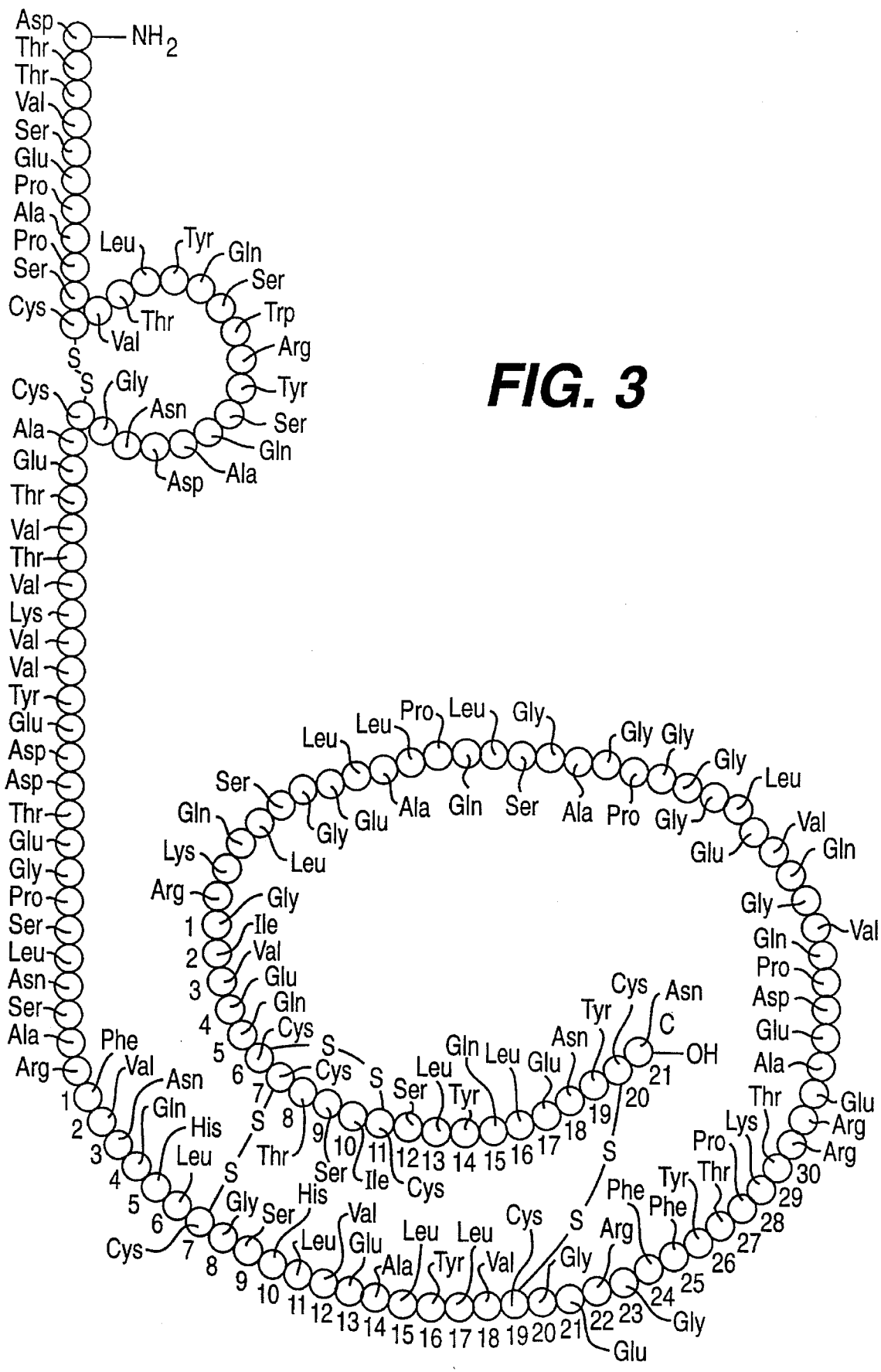
FIGS. 3 and 3a respectively depict the structural formula and amino acid sequence of refolded fusion protein PTF1.
Figure 3A:
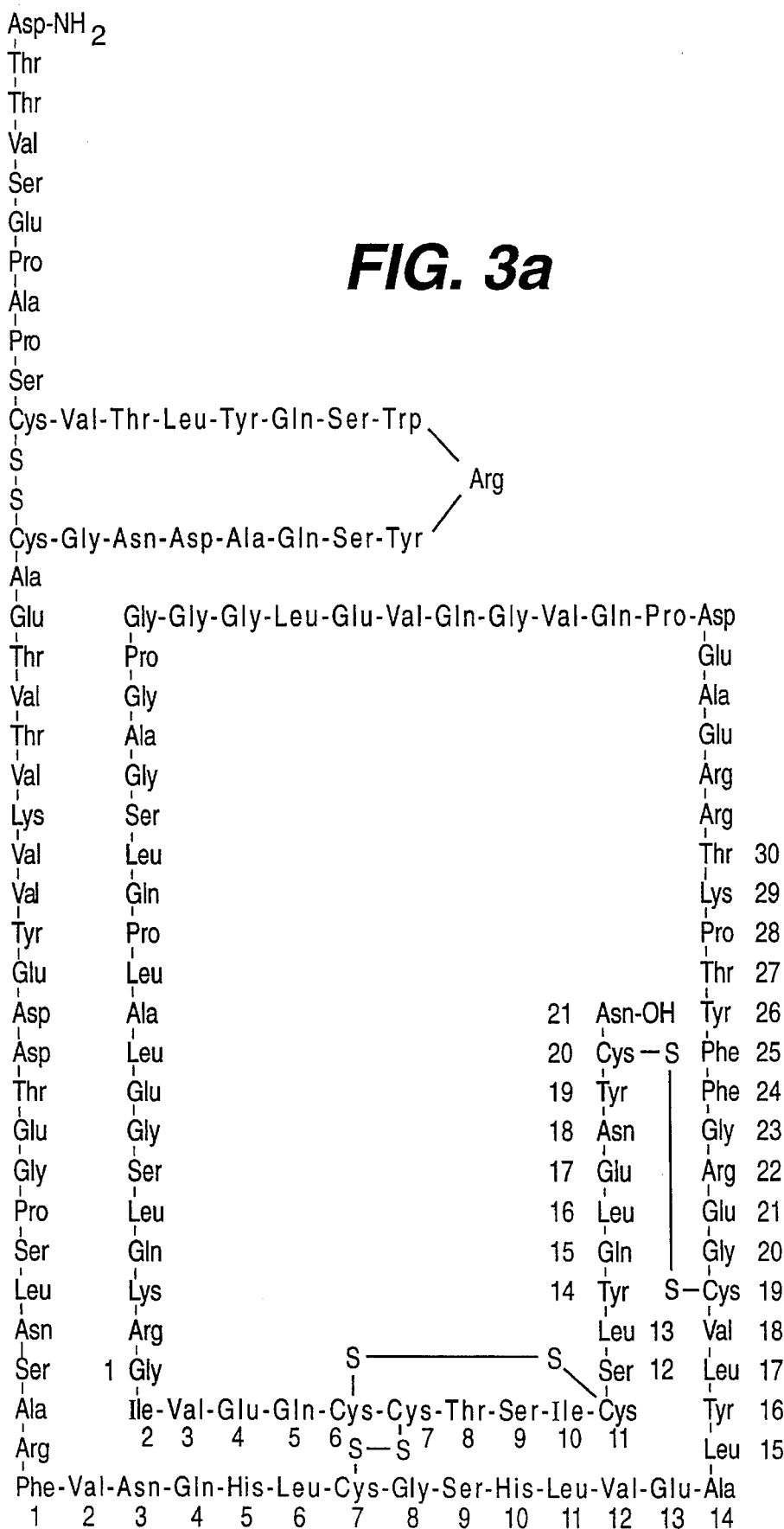

34 mg of PTF1 are dissolved in 70 ml of 8 molar urea (pH 8.6), and helium is passed through for 5 minutes. Then 760 µl of β-mercaptoethanol (pH 10.5) are added. A reduction time of 30 minutes is followed by dialysis against glycine/NaOH buffer (pH 10.5) with exclusion of oxygen for 16 hours. After this time, air is passed through and the mixture is then acidified and separated on Nucleosil 120-10 C4. The structure of the refolded product is depicted in FIG. 3 (copy=FIG. 3a). The yield is 8.2 mg, corresponding to 24% of theory.

A7) Isolation of the protein PGF4

The protein produced as in A4) is worked up in accordance with A5).

Example 1 of the Invention:

Enzymatic Cleavage of the Refolded Protein PTF1

The 8.2 mg of refolded PTF1 are dissolved in 1 ml of tris buffer (pH 8.0), and 10 µl of a solution containing 1 mg/ml lysyl endopeptidase (LEP) from Lysobacter enzymogenes is added. The solution is left to stand at room temperature for 2 hours and then again fractionated on a Nucleosil 120-5 C4 HPLC column. Yield: 3.8 mg, corresponding to 92% of theory.

The 3.8 mg of insulin precursor are dissolved in 1 ml of tris buffer (pH 8.4) and 5 µl of a solution containing 1 mg/ml trypsin are added. The reaction is stopped after 90 minutes by lowering the pH to 3.0 and separated on a Nucleosil 120-5 C4 HPLC column with the system 0.05 % trifluoroacetic acid in water/acetonitrile. Freeze-drying of the active fractions yields 2.1 mg of pure A0-Arg-de-Thr-B30-human insulin. The isoelectric point of the new material is about 6.2.

Example 2 of the Invention:

Obtaining $Arg^{A0}$, des-$Thr^{A0}$-Insulin from *E. coli* proteins

Starting material:

Fermentation of a *E. coli* strain which has been transformed with a plasmid which corresponds to the plasmid pWZIP dMdC (EP-A 0,286,956, Example 3) but codes for a proinsulin with a C chain truncated to Arg, and subsequent isolation and conversion of the protein product result in an analogous insulin precursor.

Invention:

208 mg of this material are dissolved in 100 ml of tris/HCl buffer, 0.1M (pH 8.4), and 1 mg of a lysyl endopeptidase from Lysobacter enzymogenes dissolved in the same buffer is added. The reaction is allowed to take place at room temperature for 4 hours, stirring occasionally. The reaction is checked regularly by HPLC. More than 95% of the C peptide has been eliminated after the stated time. Then 416 µl of the trypsin solution (concentration 1 mg/ml) are added to the reaction mixture, and reaction is allowed to take place for a further 3 hours. The reaction is subsequently stopped by acidification with trifluoroacetic acid, and the mixture is fractionated on a Nucleosil RP-C4 column (25 cm×4.8 cm) in the solvent system water/trifluoroacetic acid (0.1%)-acetonitrile. Freeze-drying of the insulin-containing fraction results in 88 mg of $Arg^{A0}$, des-$Thr^{B30}$-human insulin.

Preparation of $Arg^{A0}$-Human Insulin by Process Variant b):

Example 3 of the Invention:

Conversion of $Arg^{A0}$, des-$Thr^{B30}$-Insulin into $Arg^{A0}$-Insulin 13 mg of $Arg^{A0}$,des-$Thr^{B30}$-insulin obtained as in Example 1 or 2 of the invention are dissolved with 0.25 ml of 10M acetic acid and 0.65 ml of 1.54M L-threonine methyl ester in DMSO/1,3-butanediol (1:1). To this are added 150 µl of lysyl endopeptidase from Lysobacter enzymogenes (Calbiochem No. 440275), which has previously been dissolved in water (14 mg/ml). The resulting pH is about 5.3. The mixture is left to stand at room temperature for 2 hours. 94 % of the corresponding methyl ester of A0-Arg-human insulin are produced. The reaction is followed by HPLC. The protein is precipitated by addition of 1 ml of methanol and 4 ml of methyl tert.-butyl ether. The precipitate is washed once with ether and dried. To eliminate the methyl ester, the product is left to stand in 10 ml of glycine buffer, 0.1M+10 mM butylamine and pH=10.0 for a few hours.

After this, it is reprecipitated and the precipitate is taken up in 0.1% trifluoroacetic acid and purified by preparative HPLC. The pure fractions contain $Arg^{A0}$-human insulin.

We claim:

1. An essentially purified insulin derivative of the formula II

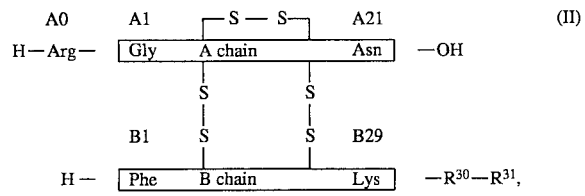

or a physiologically tolerated salt thereof, wherein a) $R^{30}$ and $R^{31}$ together are OH; or b) $R^{30}$ is a residue of a neutral, genetically encodable L-amino acid, and $R^{31}$ is OH or a physiologically acceptable organic group having 0 to 3 α-amino acids that are neutral or basic naturally occurring L-amino acids selected from the group consisting of Gly, Ala, Ser, Thr, Val, Leu, Ile, Asn, Gln, Cys, Met, Tyr, Phe, Pro, Hyp, Arg, Lys, Hyl, Orn, Cit, and His, provided that $R^{30}$ is not Ala at the same time that $R^{31}$ is OH, and further provided that the A- and B-chains are not the sequences of bovine insulin.

2. An insulin derivative and the physiologically tolerated salts thereof as claimed in claim 1, wherein in formula II $R^{30}$ and $R^{31}$ together are OH.

3. An insulin derivative and the physiologically tolerated salts thereof as claimed in claim 1, wherein for case b) in formula II $R^{30}$ is a radical of Ala, Thr, or Ser and $R^{31}$ is OH, Arg-OH, or Arg-Arg-OH.

4. An insulin derivative and the physiologically tolerated salts thereof as claimed in claim 1, wherein the A chain and the B chain (B1-B29) in formula II are the sequences of human- or, pork or beef insulin.

5. An insulin derivative as claimed in claim 1, which has an isoelectric point between 5.5 and 9.0.

6. A pharmaceutical formulation that contains an effective amount of at least one insulin derivative, or its physiologically tolerated salts, of the formula II as claimed in claim 1 in dissolved, amorphous, crystalline, or amorphous and crystalline form.

7. A pharmaceutical formulation as claimed in claim 6, which contains an effective amount of at least one of the following insulin derivatives covered by formula II (a/b):

Ar$^{A0}$, des-B30-human insulin

Arg$^{A0}$-human insulin,

Arg$^{A0}$, Arg$^{B31}$-OH-human insulin and

Arg$^{A0}$, Arg$^{B31}$, ArgB32-OH-human insulin and the physiologically tolerated salts thereof.

8. A pharmaceutical formulation as claimed in claim 6 or 7 as solution or suspension for injection having a pH of between about 3.0 and 9.0, preferably about 5.0 and 8.5.

9. A method for treating a patient suffering from diabetes mellitus, which comprises administering to said patient a pharmaceutical formulation as claimed in claim 6.

10. An insulin derivative and the physiologically tolerated salts thereof as claimed in claim 3, wherein $R^{30}$ is a radical of Thr.

11. A process for the preparation of an insulin derivative of the formula II, or its physiologically tolerated salts, as defined in claim 1, which comprises contacting with lysyl endopeptidase an insulin product of the formula III or IV

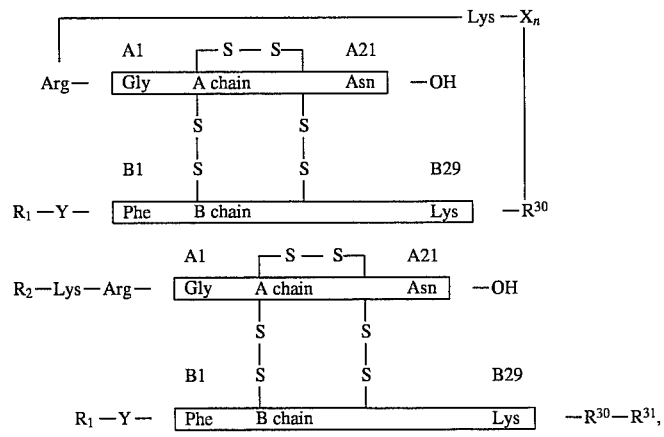

wherein

X is a residue of identical or different genetically encodable L-amino acids,

Y is Lys or Arg, n is 0 or an integer from 1 to 60, $R_1$ and $R_2$ denote hydrogen, a residue of a natural amino acid, or a peptide residue of 1 to 90 natural amino acids wherein the amino or carboxyl groups of the natural amino acids are protected or unprotected, and the A and B(1-29) chains have the sequence of human or pork insulin, to cleave the bonds at the C-terminal end of the lysyl residues, thereby forming an Arg$^{A0}$-de-B30-insulin derivative of formula II wherein $R^{30}$ and $R^{31}$ are together OH.

12. The process of claim 11, wherein $R_1$ and $R_2$ denote a peptide residue of 70 to 80 natural amino acids wherein the amino or carboxyl groups of the natural amino acids are protected or unprotected.

13. The process of claim 11, wherein when Y is Arg, the insulin product of the formula III or IV is also mixed with trypsin or a trypsin-like endopeptidase to eliminate the moiety $R_1$-Y from the B chain.

14. The process of claim 11, further comprising:

a) reacting the Arg$^{A0}$-des-B30- insulin derivative of formula II wherein $R^{30}$ and $R^{31}$ are together OH, in the presence of lysyl endopeptidase, trypsin, or a trypsin-like endopeptidase, with a compound of the formula V $$H-R^{30}-R^{31} \qquad (V),$$

wherein $R^{30}$ is a residue of a neutral, genetically encodable L-amino acid, and $R^{31}$ is OH or a physiolgically acceptable organic group having 0 to 3 α-amino acids that are neutral or basic naturally occurring L-amino acids selected from the group consisting of Gly, Ala, Set, Thr, Val, Leu, Ils, Asn, Gln, Cys, Met, Tyr, Phe, Pro, Hyp, Arg, Lys, Hyl, Om, Cit, and His, provided that $R^{30}$ is not Ala at the same time that $R^{31}$ is OH, and further provided that the A- and B-chains are not the sequences of bovine insulin, and wherein free COOH, CH, SH, NH$_2$, guanidino, or imidazole functionalities, when present, are protected by protective groups or are unprotected; and (III)

(IV)

b) eliminating said protective groups to form an insulin derivative of formula II

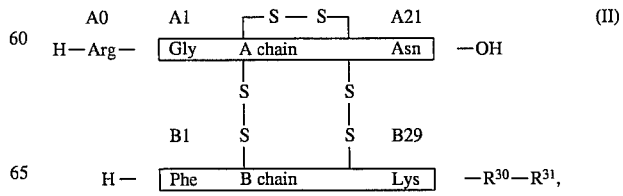

or a physiologically tolerated salt thereof.

15. A process for the preparation of an insulin derivative of the formula II, or its physiologically acceptable salts, as defined in claim 1, which comprises a) reacting an Arg$^{A0}$-des-octapeptide (B23-30)-insulin derivative of the formula VI

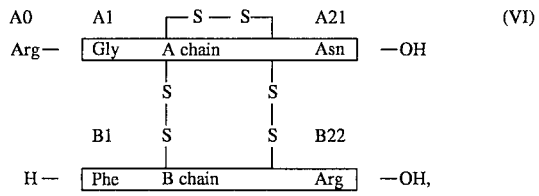

in the presence of trypsin or a trypsin-like endopeptidase, with compound of the formula VII H-Gly-Phe-Phe-Tyr-Thr-Pro-Lys-R$^{30}$-R$^{31}$ (VII)

wherein R$^{30}$ and R$^{31}$ are together OH; or

R$^{30}$ is the residue of a neutral, genetically encodable L-amino acid, and

R$^{31}$ is OH or a physiologically acceptable organic group having 0 to 3 α-amino acids that are neutral or basic naturally occurring L-amino acids selected from the group consisting of Gly, Ala, Ser, Thr, Val, Leu, Ile, Asn, Gln, Cys, Met, Tyr, Phe, Pro, Hyp, Arg, Lys, Hyl, Orn, Cit, and His, provided that R$^{30}$ is not Ala at the same time that R$^{31}$ is OH, and further provided that the A- and B-chains are not the sequences of bovine insulin, wherein free COOH, OH, SH, NH$_2$, guanidine, or imidazole functionalities, when present, are protected by protective groups or are unprotected, and b) eliminating said protective groups, when present, to form an insulin derivative of formula II,

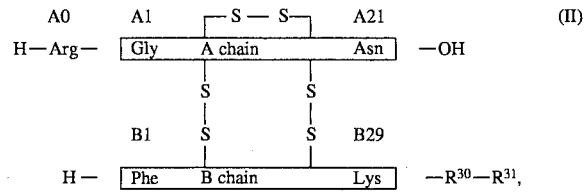

or a physiologically tolerated salt thereof.

16. A process for the preparation of an insulin derivative of the formula II, or its physiologically acceptable salts, as defined in claim 1, which comprises a) reacting an insulin derivative of the formula II'

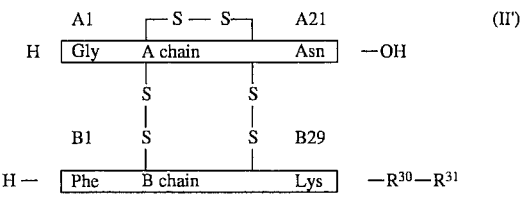

wherein

R$^{30}$ and R$^{31}$ are together OH; or

R$^{30}$ is the residue of a neutral, genetically encodable L-amino acid, and R$^{31}$ is OH or a physiologically acceptable organic group having 0 to 3 α-amino acids that are neutral or basic naturally occurring L-amino selected from the group consisting of Gly, Ala, Ser, Thr, Val, Leu, Ile, Asn, Gln, Cys, Met, Tyr, Phe, Pro, Hyp, Arg, Lys, Hyl, Orn, Cit, and His, provided that R$^{30}$ is not Ala at the same time that R$^{31}$ is OH, and further provided that the A- and B-chains are not the sequences of bovine insulin, and wherein reactive amino groups other than the amino group of Gyl$^{A1}$ are protected by protective groups, and the amino group of Gyl$^{A1}$ is unprotected, with arginine having its amino groups protected by protective groups and its carboxyl group free or in the form of an acid halide or an azide, and b) eliminating said protective groups to form an insulin derivative of formula II,

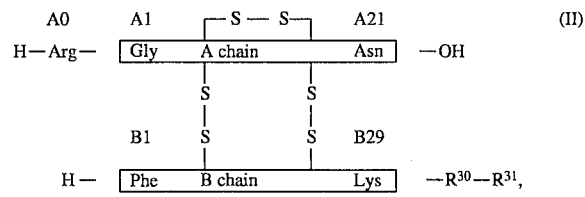

or a physiologically tolerated salt thereof.

17. A pharmaceutical formulation as claimed in claim 6, wherein the insulin derivatives or their physiologically tolerated salts are in amorphous or crystalline form.

18. pharmaceutical formulation as claimed in claim 8, wherein the solution or suspension has a pH of between about 5.0 and 8.5.

* * * * *

UNITED STATES PATENT AND TRADEMARK OFFICE
CERTIFICATE OF CORRECTION

PATENT NO. : 5,506,202
DATED : April 9, 1996
INVENTOR(S) : Laszlo Vertesy, et. al.

It is certified that error appears in the above-indentified patent and that said Letters Patent is hereby corrected as shown below:

Item [75],

Inventors, Title Page, line 1, after "László" insert a space.

Claim 4, column 13, line 8, "human-or, pork or beef" should read --human or pork--.

Claim 7, column 13, line 19, "Ar$^{40}$" should read --Arg$^{40}$--.

Claim 14, column 14, line 29, "Ils" should read --Ile--.
lines 38 and 55, callouts "(III)" and "(IV)" should be positioned flush right in column 13 with corresponding formulas.

Claim 16, column 16, line 24, "Gyl$^{A1}$" should read --Gly$^{A1}$--.
line 25, "Gyl$^{A1}$" should read --Gly$^{A1}$--.

UNITED STATES PATENT AND TRADEMARK OFFICE
CERTIFICATE OF CORRECTION

PATENT NO. : 5,506,202
DATED : April 9, 1996
INVENTOR(S) : Laszol Vertesy, et. al.

It is certified that error appears in the above-indentified patent and that said Letters Patent is hereby corrected as shown below:

Claim 18, column 16, line 44, before "pharmaceutical" insert --A--.

Signed and Sealed this

Twenty-sixth Day of August, 1997

Attest:

BRUCE LEHMAN

Attesting Officer

Commissioner of Patents and Trademarks